United States Patent [19]
McConville

[11] Patent Number: 5,826,277
[45] Date of Patent: Oct. 27, 1998

[54] SWEAT BAND

[76] Inventor: Christina H. McConville, 3120 Milhaven Lake Dr., Winston-Salem, N.C. 27106

[21] Appl. No.: 999,030

[22] Filed: Dec. 29, 1997

[51] Int. Cl.⁶ ..................................................... A42C 5/02
[52] U.S. Cl. .......................... 2/171; 2/181; 2/183; 2/184; 2/209.3; 2/DIG. 11
[58] Field of Search ........................... 2/171, 181, 181.2, 2/181.4, 183, 184, 209.3, DIG. 11

[56] References Cited

U.S. PATENT DOCUMENTS

| | | |
|---|---|---|
| 3,089,146 | 5/1963 | Sterne ........................................ 2/181 |
| 3,309,713 | 3/1967 | Kaufman .................................... 2/183 |
| 4,698,852 | 10/1987 | Romero ...................................... 2/171 |
| 5,101,516 | 4/1992 | Scarnato ................................... 2/181.2 |

*Primary Examiner*—Diana L. Biefeld
*Attorney, Agent, or Firm*—Rhodes Coats & Bennett, L.L.P.

[57] ABSTRACT

An improved sweat band. The sweat band includes an elastic band adapted to fit around a user's head and a length of sponge cloth intermittently attached along spaced apart locations to the elastic band. Only the ends and spaced apart segments of the strips are attached to the elastic band, therefore allowing the elastic band to stretch without being restricted by the inelastic sponge material. In the preferred embodiment, a tubular fabric wrap surrounds the elastic band and the length of sponge cloth to provide additional absorption and also to provide comfort to the user.

34 Claims, 2 Drawing Sheets

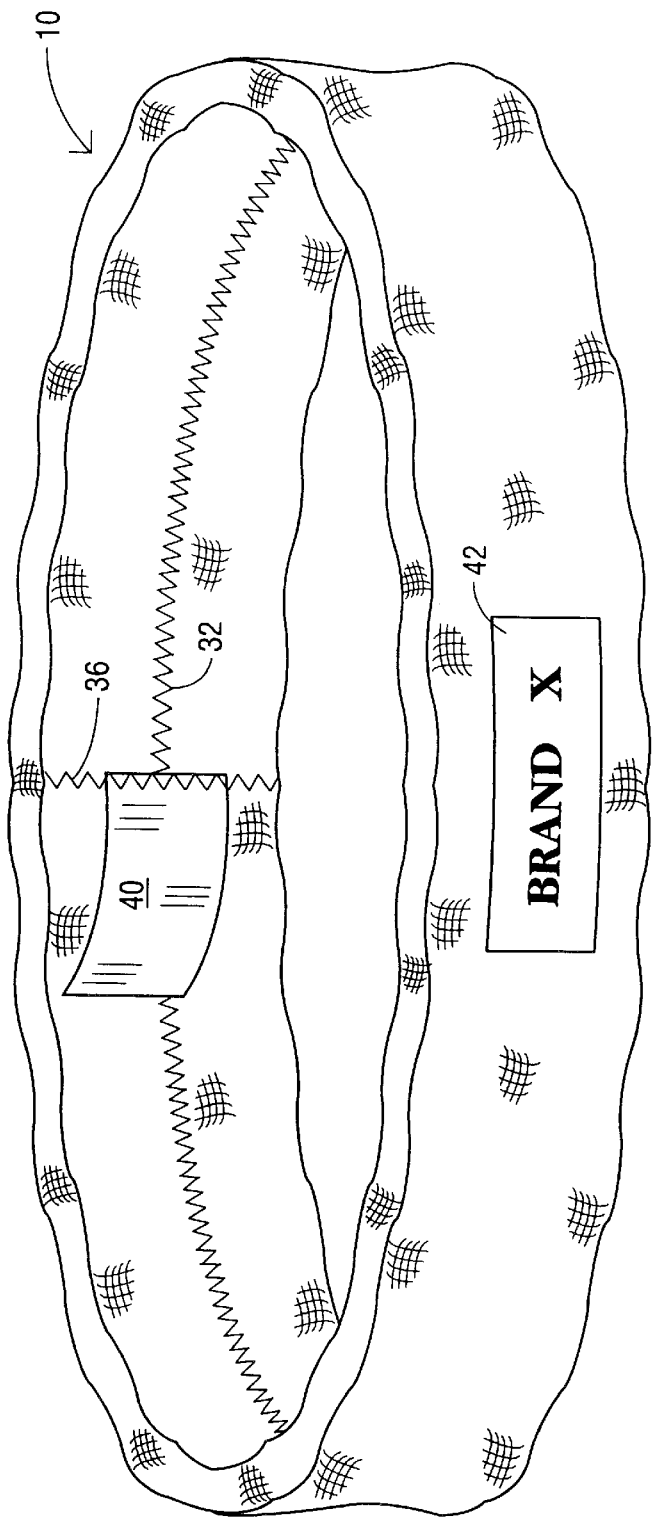
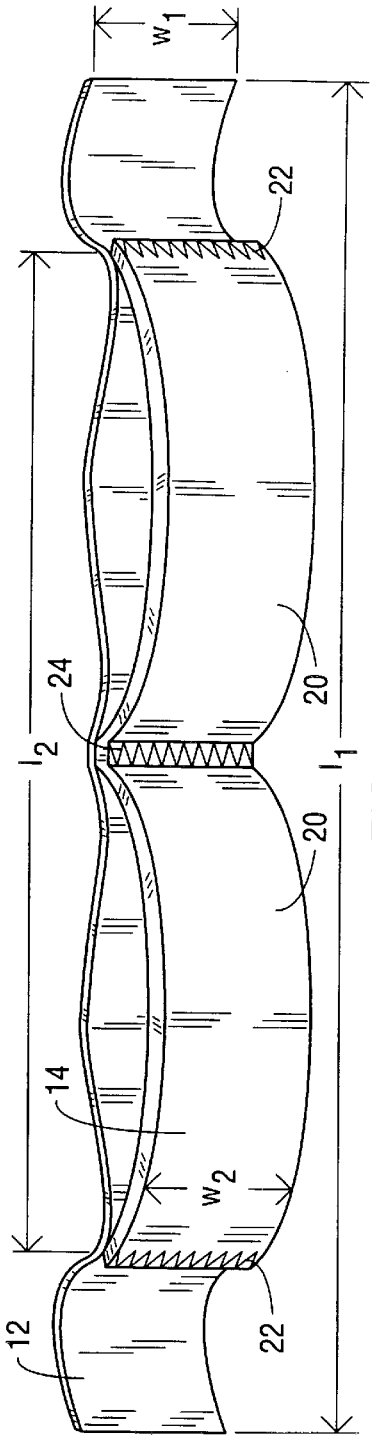

SWEAT BAND

BACKGROUND OF THE INVENTION (1) Field of the Invention the present invention relates generally to sportswear and, more particularly, to a new and improved sweat band having a much larger capacity for absorbing perspiration.

(2) Description of the Prior Art

Prior art sweat bands when formed of a solid piece of cellulose sponge or equivalent material have the disadvantage, when dry, of being inelastic. One approach to solving this problem is set forth in U.S. Pat. No. 3,089,146 to Sterne, which discloses a sweat band having a sponge material sewn into the front portion of the band and an elastic strip connecting the ends of the inelastic sponge portion.

Another approach to solving this problem is set forth in U.S. Pat. No. 5,101,516 to Searnato, which discloses a head cover, such as a cap, including a sweat band having a plurality of spaced apart "sponges".

Neither of these approaches are entirely satisfactory. Sterne limits the amount of sponge to only about ½ the distance around the head. Searnato limits the amount of sponge to small, discrete "elements". Thus, both of these approaches comprise the amount of sponge to overcome the inelastic nature of the material.

Thus, there remains a need for a new and improved sweat band which includes a much larger sponge portion which extends substantially all around the user's head while, at the same time, avoids the prior art problems in utilizing inelastic sponge materials.

SUMMARY OF THE INVENTION

The present invention is directed to an improved sweat band. The sweat band includes an elastic band adapted to fit around a user's head and a length of sponge cloth intermittently attached along spaced apart locations to the elastic band, the length of sponge cloth being sufficient to extend from about one of the user's ears to the other when the elastic band is stretched to fit the user's head.

Only the ends and spaced apart segments of the strips are attached to the elastic band, therefore allowing the elastic band to stretch without being restricted by the inelastic sponge material.

In the preferred embodiment, a tubular fabric wrap surrounds the elastic band and the length of sponge cloth to provide additional absorption and also to provide comfort to the user.

Accordingly, one aspect of the present invention is to provide a sweat band for absorbing perspiration. The sweat band includes: (a) an elastic band adapted to fit around a user's head; and (b) a length of sponge cloth intermittently attached along spaced apart locations to the elastic band.

Another aspect of the present invention is to provide a sponge cloth strip assembly for a sweat band having an elastic band adapted to fit around a user's head. The sponge cloth strip assembly includes: a length of sponge cloth intermittently attached along spaced apart locations to the elastic band, the length of sponge cloth being sufficient to extend from about one of the user's ears to the other when the elastic band is stretched to fit the user's head.

Still another aspect of the present invention is to provide a sweat band for absorbing perspiration. The sweat band includes: (a) an elastic band adapted to fit around a user's head; (b) a length of sponge cloth intermittently attached along spaced apart locations to the elastic band, the length of sponge cloth being sufficient to extend from about one of the user's ears to the other when the elastic band is stretched to fit the user's head; and (c) a tubular fabric wrap surrounding the elastic band and the length of sponge cloth.

These and other aspects of the present invention will become apparent to those skilled in the art after a reading of the following description of the preferred embodiment when considered with the drawings.

BRIEF DESCRIPTION OF THE DRAWINGS

FIG. 1 is a perspective view of a sweat band constructed according to the present invention;

FIG. 2 is a perspective view of the sponge cloth being attached to the elastic band;

DESCRIPTION OF THE PREFERRED EMBODIMENTS

Figure 3:
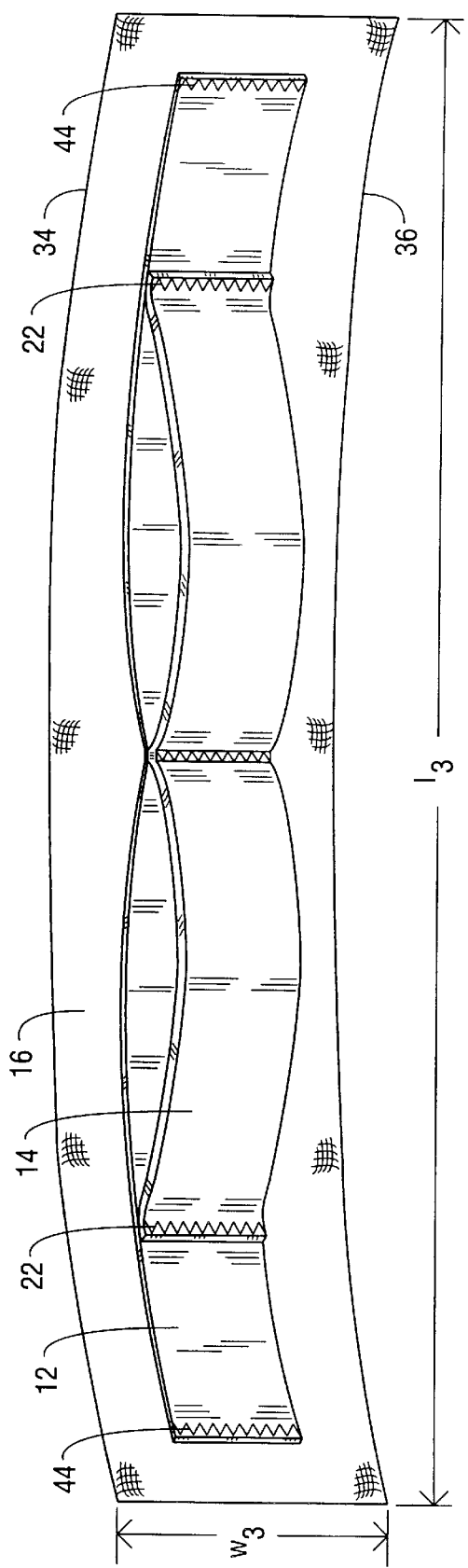
FIG. 3 is a perspective view of the embodiment shown in FIG. 2 illustrating the elastic band being attached to the fabric wrap.

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIG. 1, a sweat band, generally designated 10, is shown constructed according to the present invention. The sweat band 10 is comprised of an elastic band 12 capable of stretching and retracting to hold the band onto a user's head, a sponge cloth 14 attached at a limited number of spaced apart positions along its length to the elastic band for absorbing perspiration and an exterior fabric wrap 16 for absorbing perspiration and providing a comfortable feel to the user.

The elastic band 12 is adapted to fit around the user's head and can be stretched to fit a variety of users and circumstances. When the sweat band is worn, the elastic is stretched to fit around the user's head and biases to hold the sweat band in a relatively fixed position on the user during physical exertions such as running, gardening, playing basketball, and other activities. The elastic band 12 allows the sweat band to be firmly placed on the user's forehead to catch perspiration and preventing it from running into the user's face and eyes.

The elastic band 12 is preferably constructed of a sports type elastic which has a softer, more comfortable feel when worn. In one embodiment of the present invention, the elastic band measures 20 inches in its resting or non-stretched orientation illustrated as $l_1$, as shown in FIG. 2. The elastic band can then be stretched to approximately 36 inches, which is about 180% of its starting, untensioned length. As the average adult human head measures about 25 inches in circumference, this length of elastic band is sufficient to adequately fit most users. In the preferred embodiment, the elastic band 12 is between about ¾ to 1½ inches in width as illustrated by $w_1$ in FIG. 2. Preferably, the width is about 1¼ inches.

Figure 4:
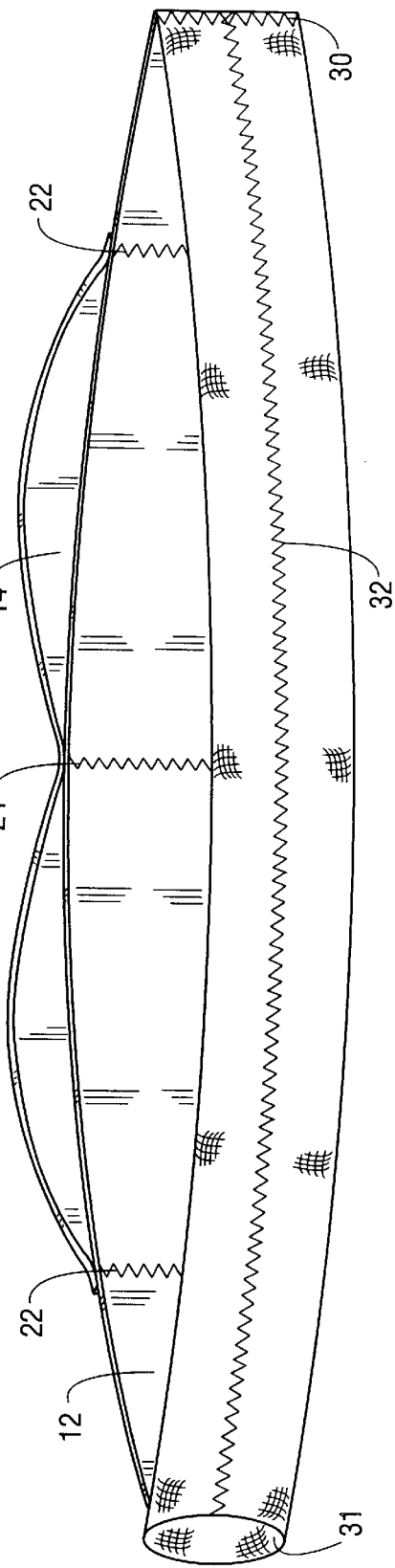
FIG. 4 is a rear perspective view illustrating the fabric wrap being connected in a folded arrangement attached to the elastic band and sponge cloth.

A sponge cloth 14 is attached at spaced apart locations to the elastic band as shown in FIGS. 2, 3 and 4. The sponge cloth 14 provides for additional perspiration absorption without adding a great deal of bulk or weight to the sweat band. In the preferred embodiment, the sponge cloth is constructed of a cellulose material, such as $C_6H_{10}O_5$. One example of the sponge cloth is manufactured by Spontex, Incorporated, Columbia, Tenn.

Preferably, the sponge cloth 14 is sized to extend across about one-half of the circumference of the user's head. For example, when the sweat band is worn, the sponge cloth extends across the user's forehead from ear to ear, which is about 12 inches. The width $w_2$ of the sponge cloth is between about ¾ and 1½ inches and preferably about 1¼ inches. The width dimension of the sponge cloth is somewhat smaller than the width of the elastic band providing for the cloth to be contained within the band.

The sponge cloth is attached to the elastic band at intermittent, spaced apart locations along its length. The cloth is placed on the elastic band intermittently because the cloth has a smaller elasticity and does not stretch to the same extent that the band stretches.

In one embodiment, the sponge cloth is attached to the elastic band at its center 24 and at each end 22. The center connection 24 is placed about the center of the elastic band. Each end of the sponge cloth is then attached approximately 5 inches apart from the center leaving about 1 inch of slack in the length of the sponge between the two connection points. The slack, illustrated as 20 in FIG. 2, is necessary because as the elastic band 12 stretches the slack is taken out resulting in the sponge cloth being pulled into contact with the band.

The intermittent, spaced apart attachment allows for the sweat band to stretch and retract even though there is little or no stretch in the sponge cloth when dry. It will be understood that there are alternative designs of intermittently tacking the sponge cloth to the elastic band, such as tacking every 2 inches off-center, every 3 inches off-center, etc.

Another advantage for attaching the sponge cloth to the elastic band is to insure the sweat band maintains its shape and form during the washing process. The intermittent tacking of the sponge cloth insures it maintains its position on the elastic band during a washing machine and dryer cycle.

In the preferred embodiment, a fabric wrap 16 forms the exterior layer of the sweat band. The fabric wrap functions to absorb perspiration from the user and also provides a soft, comfortable feel to the user. In one embodiment, the fabric wrap is 100% cotton or a cotton/polyester combination such as a terry cloth material. The fabric wrap 16 is a substantially rectangular shape between about 28–32 inches in length $l_3$ and preferably about 30 inches long. The width $w_3$ is between about 4–6 inches and preferably 4¾ inches wide.

The fabric wrap is formed into a tubular arrangement as shown in FIG. 4. The upper and lower edges 34, 36 of the fabric wrap are joined together by a seam 32 and an in-seam 30 to form the tubular construction. The elastic band 12 and sponge cloth 14 are then pulled into the tubular fabric wrap. This configuration provides for an aesthetically pleasing appearance and a more comfortable feel for the user as the elastic and sponge do not directly contact the user but are contained within the fabric wrap. The ends of the fabric wrap 30, 31 are then tacked together to form one continuous band 36 shown in FIG. 1.

In use, seam 32 is positioned toward the user and is not visible while the sweat band is being worn. Additionally, seam 36 may further contain a tag 40 for washing instructions or other information. The exterior edge of the sweat band 42 that is visible on the forehead of the user while being worn may further include indicia such as a trademark or design.

Each of the seams that connects the elastic band 12, sponge cloth 14 and fabric wrap 16 are constructed to be durable but non-bulky. An advantage of the sweat band design is that each seam is located at a different point along the length of the sweat band and no two vertical seams are positioned in the same place. Only seam 32 overlaps another seam as this seam runs the entire horizontal length of the sweat band. By way of example, the seams that attach the sponge cloth 14 to the elastic band 12 illustrated as 22 and 24 are located at a different point then the attachments of the elastic band to the fabric wrap illustrated as 44. This disbursement of attachment seams throughout the length provide for additional comfort.

In the preferred embodiment, the sweat band 10 is constructed of lightweight materials for increased comfort without diminished absorption ability. The elastic band 12 weighs about 0.25 ounces, the sponge cloth weighs about 0.20 ounces, and the fabric wrap weighs about 1.10 ounces for a combined total of 1.5 ounces for the entire sweat band. The sweat band is able to absorb approximately 6 to 8 ounces of perspiration as the 30 inch length of fabric wrap is able to absorb about ½ cup of perspiration, and a twelve inch length of sponge cloth is able to absorb about ⅛ to ¼ cup of perspiration for a combined absorption amount of approximately six to eight ounces. The amount of perspiration absorbed by the elastic band is negligible. The gradual absorbtion is greater.

As shown above, the sweat band is constructed of materials that can be cleaned and dried in a home washing machine and dryer without deleterious effects. The materials of the sweat band and construction is durable to withstand this treatment numerous times without failing.

Certain modifications and improvements will occur to those skilled in the art upon a reading of the foregoing description. It should be understood that all such modifications and improvements have been deleted herein for the sake of conciseness and readability but are properly within the scope of the following claims.

I claim:

1. A sweat band for absorbing perspiration, said sweat band comprising:

(a) an elastic band adapted to fit around a user's head; and (b) a length of sponge cloth intermittently attached along spaced apart locations to said elastic band.

2. The sweat band according to claim 1, further including a tubular fabric wrap surrounding said elastic band and said length of sponge cloth.

3. The sweat band according to claim 2, wherein said tubular fabric wrap is formed from terry cloth.

4. The sweat band according to claim 3, wherein said terry cloth is between about 50 to 100% cotton.

5. The sweat band according to claim 2, wherein said tubular fabric wrap is between 28 and 32 inches in length to loosely fit about the user's head.

6. The sweat band according to claim 5, wherein said tubular fabric wrap is about 30 inches in length to loosely fit about the user's head while allowing about 5 inches in length for gather.

7. The sweat band according to claim 2, wherein said tubular fabric wrap is formed from an absorbent, lightweight material.

8. The sweat band according to claim 7, wherein said absorbent, lightweight material is about 1.1 oz for a 30 inch length and can absorb about ¾ cup of perspiration which is about 5 times its weight.

9. The sweat band according to claim 1, wherein said elastic band is about 20 inches in length untensioned to fit about the user's head.

10. The sweat band according to claim 9, wherein said elastic band will stretch to about 36 inches to fit about the user's head while allowing about 11 inches in length for tension.

11. The sweat band according to claim 1, wherein said elastic band is between ¾ and 1½ inches in width to fit about the user's head without twisting.

12. A sponge cloth strip assembly for a sweat band having an elastic band adapted to fit around a user's head, said sponge cloth strip assembly comprising: a length of sponge cloth intermittently attached along spaced apart locations to said elastic band, said length of sponge cloth being sufficient to extend from about one of the user's ears to the other when said elastic band is stretched to fit the user's head.

13. The sweat band according to claim 12, wherein said sponge cloth is formed from an absorbent, lightweight cellulose material.

14. The sweat band according to claim 13, wherein said absorbent, lightweight cellulose material is about 0.2 oz for a 12 inch length and can absorb about ¼ cup of perspiration which is about 10 times its weight.

15. The sweat band according to claim 12, wherein said sponge cloth is about 12 inches in length to extend from one of the user's ears to the other.

16. The sweat band according to claim 12, wherein said sponge cloth is between ¾ and 1½ inches in width to fit about the user's head without twisting.

17. The sweat band according to claim 12, wherein said sponge cloth intermittently attached along spaced apart locations to said elastic band is attached at its ends to said elastic band.

18. The sweat band according to claim 12, wherein said sponge cloth intermittently attached along spaced apart locations to said elastic band is attached at its ends to said elastic band and in at least in its middle, said sponge cloth being attached to said elastic band in gathers such that when said elastic band is stretched to fit the user, said elastic band and said sponge cloth are about the same length.

19. A sweat band for absorbing perspiration, said sweat band comprising:

(a) an elastic band adapted to fit around a user's head;

(b) a length of sponge cloth intermittently attached along spaced apart locations to said elastic band, said length of sponge cloth being sufficient to extend from about one of the user's ears to the other when said elastic band is stretched to fit the user's head; and (c) a tubular fabric wrap surrounding said elastic band and said length of sponge cloth.

20. The sweat band according to claim 19, wherein said tubular fabric wrap is formed from terry cloth.

21. The sweat band according to claim 20, wherein said terry cloth is between about 50 to 100% cotton.

22. The sweat band according to claim 19, wherein said tubular fabric wrap is between 28 and 32 inches in length to loosely fit about the user's head.

23. The sweat band according to claim 22, wherein said tubular fabric wrap is about 30 inches in length to loosely fit about the user's head while allowing about 5 inches in length for gather.

24. The sweat band according to claim 19, wherein said tubular fabric wrap is formed from an absorbent, lightweight material.

25. The sweat band according to claim 24, wherein said absorbent, lightweight material is about 1.1 oz for a 30 inch length and can absorb about ¾ cup of perspiration which is about 5 times its weight.

26. The sweat band according to claim 19, wherein said elastic band is about 20 inches in length untensioned to fit about the user's head.

27. The sweat band according to claim 26, wherein said elastic band will stretch to about 36 inches to fit about the user's head while allowing about 11 inches in length for tension.

28. The sweat band according to claim 19, wherein said elastic band is between ¾ and 1½ inches in width to fit about the user's head without twisting.

29. The sweat band according to claim 19, wherein said sponge cloth is formed from an absorbent, lightweight cellulose material.

30. The sweat band according to claim 29, wherein said absorbent, lightweight cellulose material is about 0.2 oz for a 12 inch length and can absorb about ¼ cup of perspiration which is about 10 times its weight.

31. The sweat band according to claim 19, wherein said sponge cloth is about 12 inches in length to extend from one of the user's ears to the other.

32. The sweat band according to claim 19, wherein said sponge cloth is between ¾ and 1½ inches in width to fit about the user's head without twisting.

33. The sweat band according to claim 19, wherein said sponge cloth intermittently attached along spaced apart locations to said elastic band is attached at its ends to said elastic band.

34. The sweat band according to claim 19, wherein said sponge cloth intermittently attached along spaced apart locations to said elastic band is attached at its ends to said elastic band and in at least in its middle, said sponge cloth being attached to said elastic band in gathers such that when said elastic band is stretched to fit the user, said elastic band and said sponge cloth are about the same length.

\* \* \* \* \*